United States Patent
Lechot et al.

(10) Patent No.: US 7,011,662 B2
(45) Date of Patent: Mar. 14, 2006

(54) SURGICAL REAMER

(75) Inventors: André Lechot, Orvin (CH); Patrick White, Downingtown, PA (US)

(73) Assignee: Precimed SA, Orvin (CH)

( * ) Notice: Subject to any disclaimer, the term of this patent is extended or adjusted under 35 U.S.C. 154(b) by 108 days.

(21) Appl. No.: 10/450,771

(22) PCT Filed: Dec. 21, 2001

(86) PCT No.: PCT/IB01/02676

§ 371 (c)(1),
(2), (4) Date: Jun. 17, 2003

(87) PCT Pub. No.: WO02/49517

PCT Pub. Date: Jun. 27, 2002

(65) Prior Publication Data
US 2004/0049199 A1    Mar. 11, 2004

(30) Foreign Application Priority Data
Dec. 21, 2000   (CH) ..................................... 2500/00

(51) Int. Cl.
*A61B 17/32* (2006.01)
(52) U.S. Cl. ...................................................... 606/80
(58) Field of Classification Search ................ 606/79, 606/80, 81, 167, 180, 183
See application file for complete search history.

(56) References Cited

U.S. PATENT DOCUMENTS

| | | | |
|---|---|---|---|
| 3,630,204 A * | 12/1971 | Fishbein .................... | 606/81 |
| 3,633,583 A * | 1/1972 | Fishbein .................... | 606/81 |
| 3,702,611 A * | 11/1972 | Fishbein .................... | 606/81 |
| 5,084,052 A * | 1/1992 | Jacobs ....................... | 606/79 |
| 5,290,315 A | 3/1994 | DeCarlo | |
| 5,299,893 A | 4/1994 | Salyer et al. | |
| 5,658,290 A | 8/1997 | Takebayashi et al. | |
| 5,755,719 A * | 5/1998 | Frieze et al. ............... | 606/81 |
| 5,897,558 A | 4/1999 | Frieze et al. | |
| 5,957,368 A | 9/1999 | Takebayashi et al. | |
| 6,106,536 A * | 8/2000 | Lechot ....................... | 606/180 |
| 6,322,564 B1 * | 11/2001 | Surma ........................ | 606/79 |

FOREIGN PATENT DOCUMENTS

| | | | |
|---|---|---|---|
| DE | 1566114 | * | 10/1970 |
| EP | 0 704 121 | | 11/1995 |
| EP | 0704191 | | 4/1996 |
| EP | 0782890 | | 1/1997 |
| EP | 0947170 A | | 10/1999 |
| FR | 1031888 A | | 6/1953 |
| FR | 2233972 | * | 1/1975 |
| FR | 2233972 A | | 1/1975 |
| FR | 2281025 | | 2/1976 |

* cited by examiner

*Primary Examiner*—Eduardo C. Robert
*Assistant Examiner*—Annette Reimers
(74) *Attorney, Agent, or Firm*—Moetteli & Associes Sarl; John Moetteli (57) ABSTRACT

A low insertion profile surgical reamer for cutting a bone socket comprises a cutting structure. The cutting structure is rotatable about a longitudinal axis. The structure has a static profile area upon insertion of the reamer into the bone socket and a dynamic profile area generated upon rotation, both profile areas lying transverse to the axis. The static profile area is substantially smaller than the dynamic profile area. The reamer includes centrally located holes, allowing it to be fixed to a tool holder.

31 Claims, 11 Drawing Sheets

SURGICAL REAMER

BACKGROUND OF THE INVENTION

The subject of this invention is a surgical reamer fitted with a device allowing it to be fixed to a tool holder so that it can be driven in rotation and with at least one cutting edge made up of the edge of a plate containing the reamer's rotary axis.

A reamer of this sort is known under U.S. Pat. Nos. 3,633,583 and 5,290,315. On these reamers, the cutting edge is formed on a half-disk inserted into a diametric split made in a monolithic head which is noticeably hemispherical. The disk is held in the head by a screw and the head has gashes, like a drill bit, for the formation of shavings. In operation, there is an increased risk of these reamers becoming off centre due to the lack of homogeneity of the osseous matter.

From document EP 0 947 170, the content of which is incorporated herein by reference, a surgical reamer is shown, particularly intended for the processing of the cotyloid cavity when replacing the hip joint with a total prosthesis, in the shape of a revolving hollow body, in particular a hemispherical cap stretching from one side of the rotary axis and whose edge, over half of its circumference, constitutes the cutting edge. The surface of the cap itself may be fitted with teeth as with reamers of the rasp type which are commonly seen in previous practice, as described, for instance, in patents FR 2 281 025, EP 0 704 121 and 0 782 890, the content of which is incorporated herein by reference. However, it is very difficult to form an exact hemisphere using the usual processes, such as stamping.

What is needed is a surgical reamer allowing the centring to be maintained whilst in operation, using simple means. In addition, what is needed is a reamer that has a small insertion profile, compared to its swept cutting area.

SUMMARY OF THE INVENTION

A surgical reamer according to the invention has a cutting structure rotatable about a longitudinal axis. The structure has a static profile area upon insertion of the reamer into the bone socket and a dynamic profile area generated upon rotation, both profile areas lying transverse to the axis. The static profile area is substantially smaller than the dynamic profile area. The reamer includes centrally located holes (18), allowing it to be fixed to a tool holder. The invention therefore has a low insertion profile permitting entry into an incision of a relatively small size.

The reamer form may be spherical, conical or of some other shape. At least one cutting edge can be fitted with teeth.

According to the preferred mode of production for the invention, the reamer is made up of two plates which are split down the middle according to their axis of symmetry and housed at right angles to and inside one another. This is particularly simple to manufacture and also stands out due to its good rigidity and by how easy it is to clean.

The plates constitute the cutting structure. The plates are angularly arranged around the rotary axis in such a way as to form three edges including at least one which is a cutting edge. The distribution of at least three edges around the rotary axis ensures that centring is maintained during milling. If only one of the edges is a cutting edge, the other edges are used only for guiding, that is to say for maintaining the centring.

The disk, whose split leads out onto the top of the reamer, can usefully be cut so as to release the profile of the other disk at the top and thus allow a cut in the centre when milling.

The plates have holes used for fixing the reamer onto a tool holder or an adapter with a head fitted with frontal slots extending radially in relation to the support axis and oriented in such a way as to allow them to house the reamer plates. The devices used to hold the reamer in the slots are usefully made up of balls which engage in the holes on the reamer's plates and a ball locking device keeping the balls engaged in the holes in the plates.

BRIEF DESCRIPTION OF THE DRAWINGS

As an example, the appended drawing shows a mode for producing the invention.

DETAILED DESCRIPTION OF THE INVENTION

Figure 1:
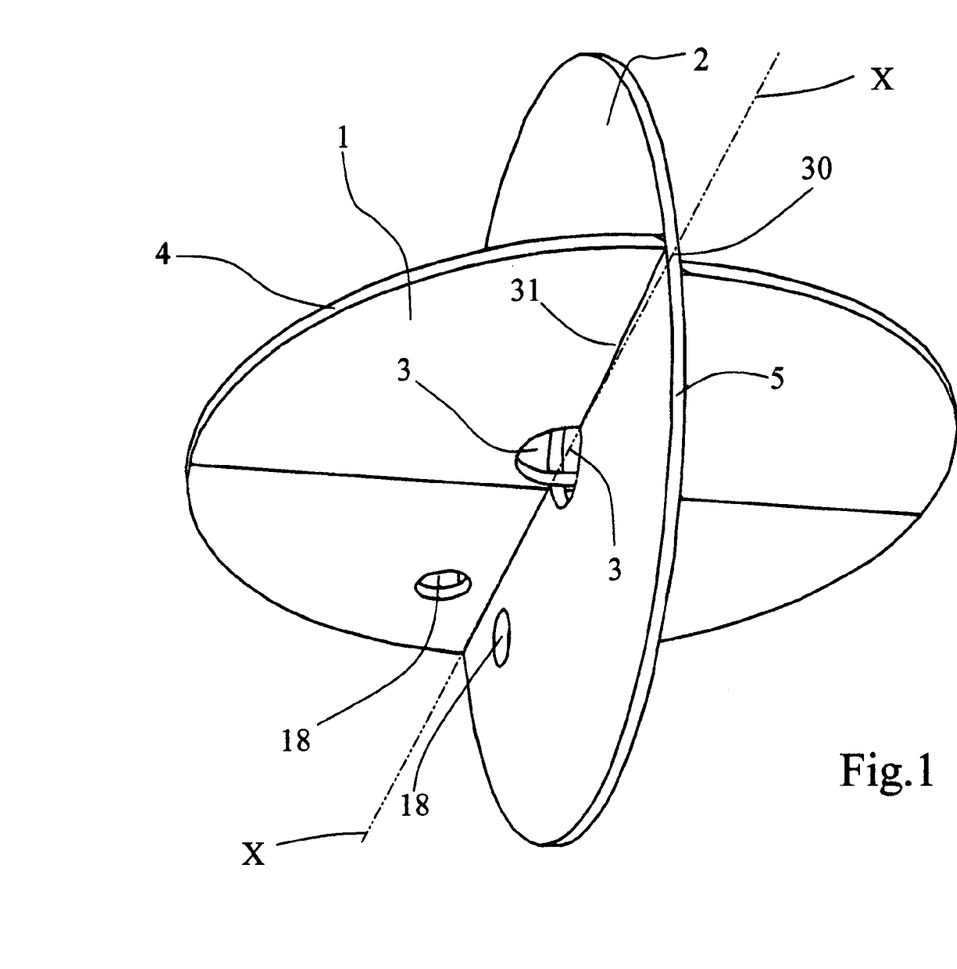
FIG. 1 is a perspective view of the reamer.

The reamer shown in FIG. 1 is made up of two disks or plates 1 and 2 perpendicularly assembled. The plates 1 and 2 make up a cutting structure 50. The cutting structure 50 is rotatable about a longitudinal axis X—X when mounted to a holder 6.

For this purpose, the plates are split down the middle, that is to say according to a radius leading into a central circular cut 3 and they are housed in one another by means of these slots and laser welded so as to give a spherical case of which edges 4 and 5 make up meridians. Edges 4 and 5 present sharp edges forming cutting edges.

In the example shown, disk 1 has a split which leads to the top 30 of the reamer and is cut so that the sides of its split 31 diverge from one another on the plane of the other disk 2, on both sides of the reamer's rotary axis X—X. The effect of this is to release the edges of the disk 2 at the top 30 and to thus allow a centre cut when milling.

Figure 2A:
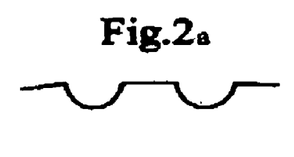
FIGS 2a–2c shows three examples of teeth formed on the disks.
Figure 2B:
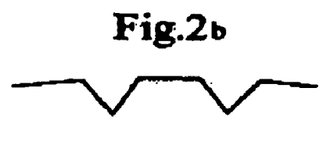
Figure 2C:
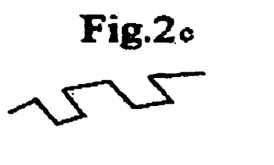
Figure 3A:
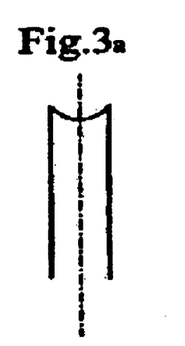
FIGS. 3a–3i show examples of disk cutting profiles.
Figure 3B:
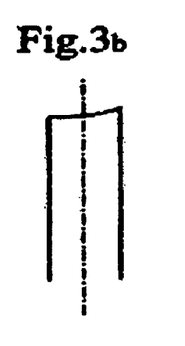
Figure 3C:
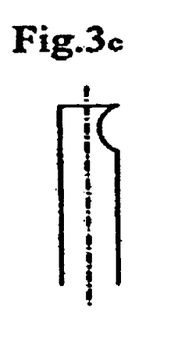
Figure 3D:
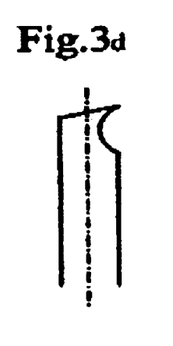
Figure 3E:
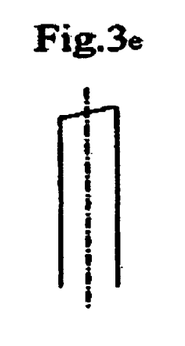
Figure 3F:
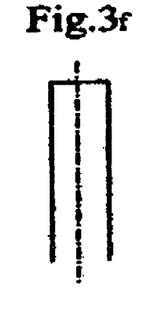
Figure 3G:
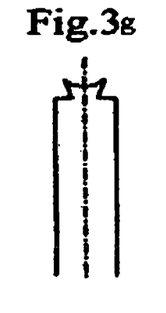
Figure 3H:
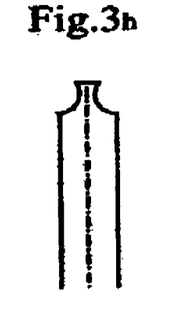
Figure 3I:
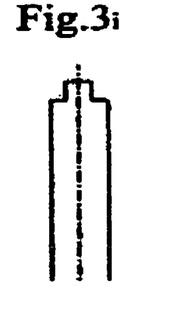

At least one of the edges 4, 5 of the plates can be fitted with cutting teeth. Examples of teeth shapes are shown in FIG. 2, either teeth in a U shape (a), an "N" shape (b) or sloping slot teeth (c). The four edges of the reamer should preferably be fitted with teeth and these teeth are offset, respectively alternated, from one disk to the other or from one half-disk to the next, in relation to the trajectory of these teeth, so as to obtain a full sweep, without grooves, when milling a spherical cavity.

The cutting edges 4 and 5 may show various cutting profiles examples of which are shown in FIG. 3
  a) half-moon profile on the topside,
  b) elliptical profile generating a positive cut,
  c) half-moon profile on the cutting side of the plates with a neutral cutting angle
  d) half-moon profile on the cutting side of the plates with a positive cutting angle
  e) diagonal profile generating a positive cutting angle,
  f) neutral profile,
  g) half-moon profile on the topside with two relief angles per disk,
  h) half-moon profile on both sides of the plates,
  i) tenon profile which can synthesise profiles a} to h}.

A reamer of this sort cannot be fixed directly onto a tool holder as described in the applicant's patent EP 0 704 191 (U.S. Pat. No. 5,658,290), the content of which is incorporated by reference herein, which has a head intended to house a cross held by a bayonet fixture. In order to be able to use the same tool holder for reamers fitted with a fixing cross, the new reamer is fixed onto an adapter 6 shown in FIGS. 4 to 8. This adapter could obviously constitute a full tool holder.

The holder 6 has a cylindrical body 7 fitted, at one end, with a head 8 designed to house the reamer and, at the other end, with a fixing cross made up of four cylindrical branches 9 forced radially through the body 7. The head 8, generally cylindrical in shape, is split diametrically so as to have four slots 10 which are at right angles to one another, whose width corresponds to the thickness of plates 1 and 2. These slots 10 are limited on one side by a relatively thin wall 11 and, on the other side, by a rather thicker wall 12. The walls 12 are pierced by a circular hole 13, which is cylindrical over most of the walls. The balls 14, whose diameter is greater than the thickness of the walls 12 are held in these holes. These balls 14 can also be moved into the holes 13 50 as to release the slots 10 or not.

Figure 7:
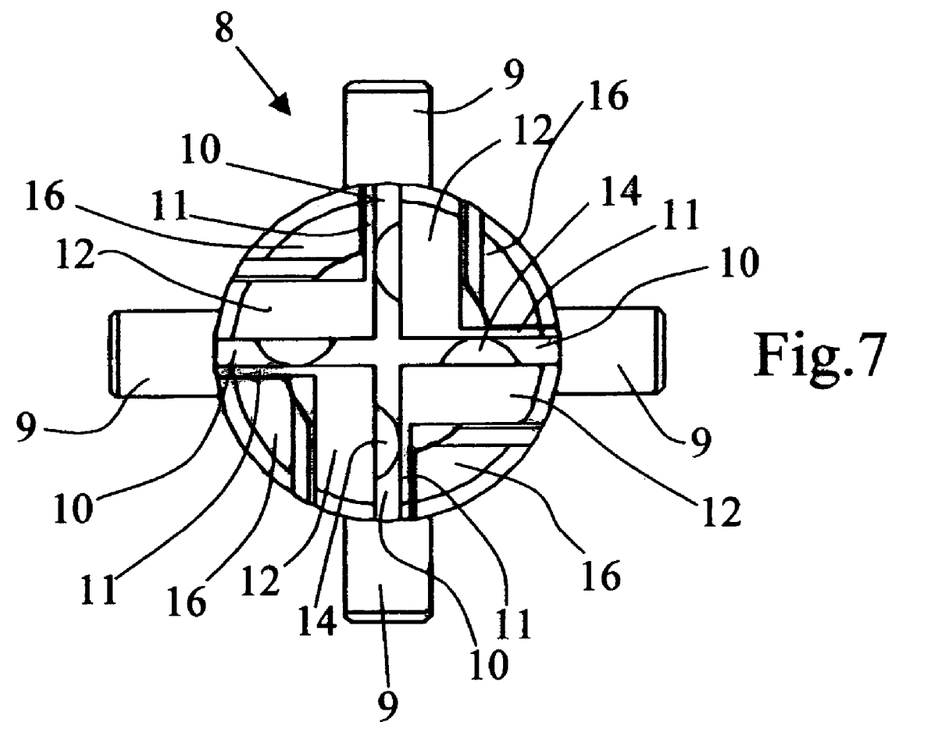
FIG. 7 is an axial view of the adapter.
Figure 8:
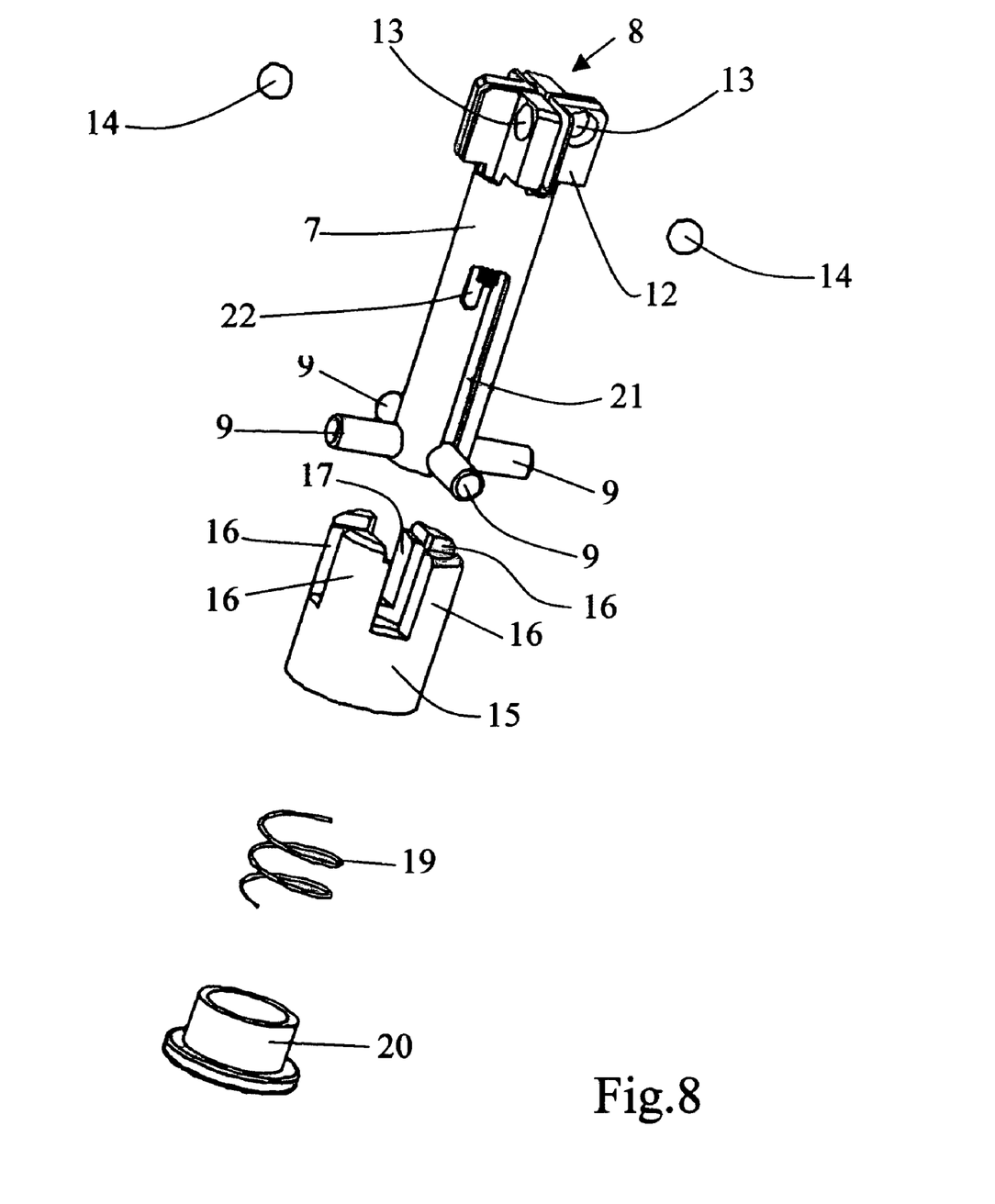
FIG. 8 is an exploded view of the adapter.

A locking ring 15, with four pins 16 is mounted, sliding, onto the body 7 stretching out in parallel to the axis of the ring. These pins 16 are engaged in the head 8, more precisely in the spaces left free by the walls 11 and 12. Each of these pins 16 has one flat side 17 which at least approximately slides onto the side of a wall 12 opposite the corresponding split 10, so as to keep the corresponding ball engaged in the split 10, as shown in FIG. 7. If the reamer is engaged in the slots 10, the balls 14 are then engaged in the holes 18 on plates 1 and 2 so that the reamer is held onto the head 8.

Figure 4:
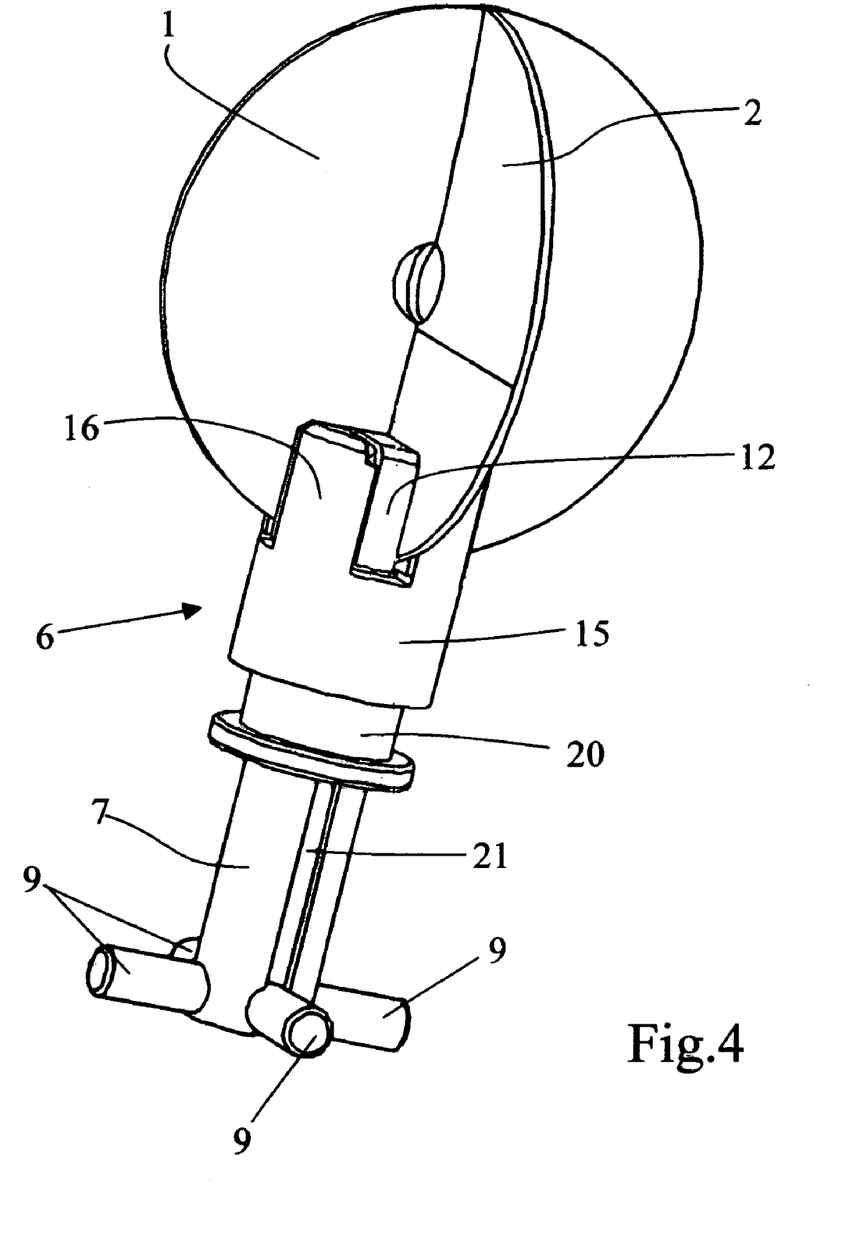
FIG. 4 shows the same reamer mounted on an adapter.
Figure 5:
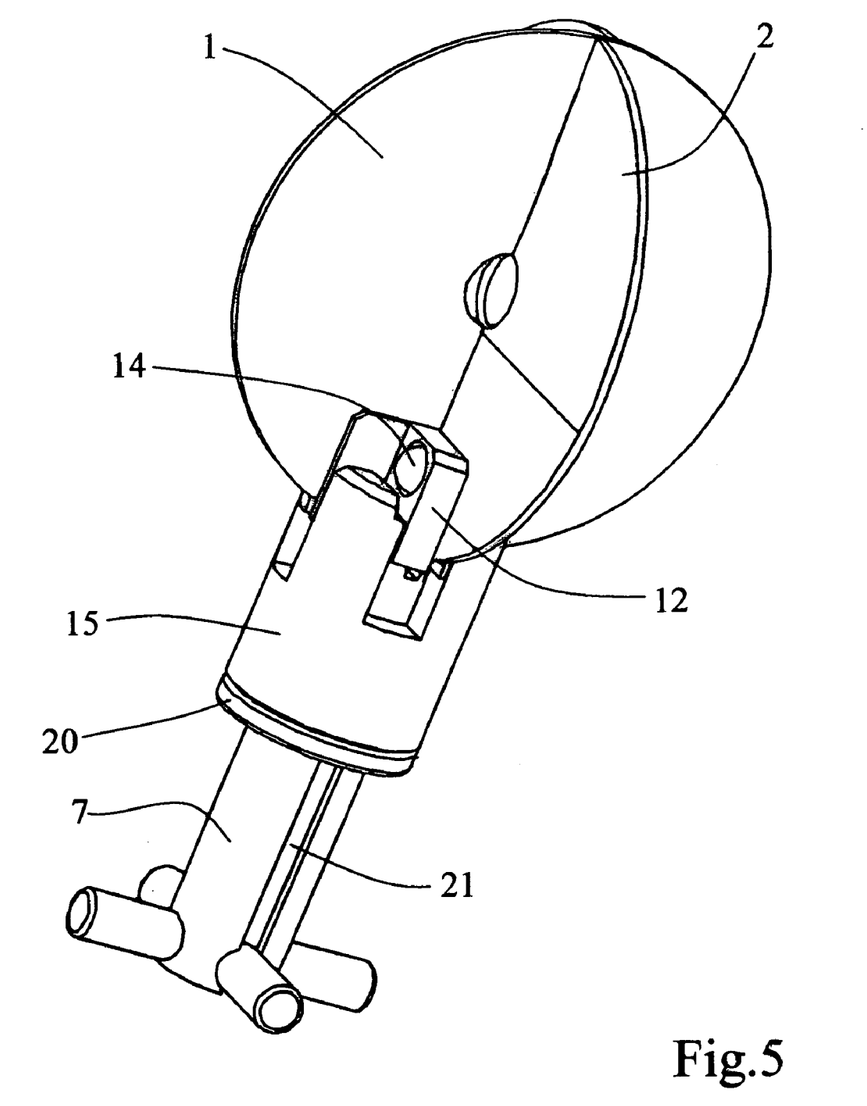
FIG. 5 shows the adapter in the reamer release position.
Figure 6:
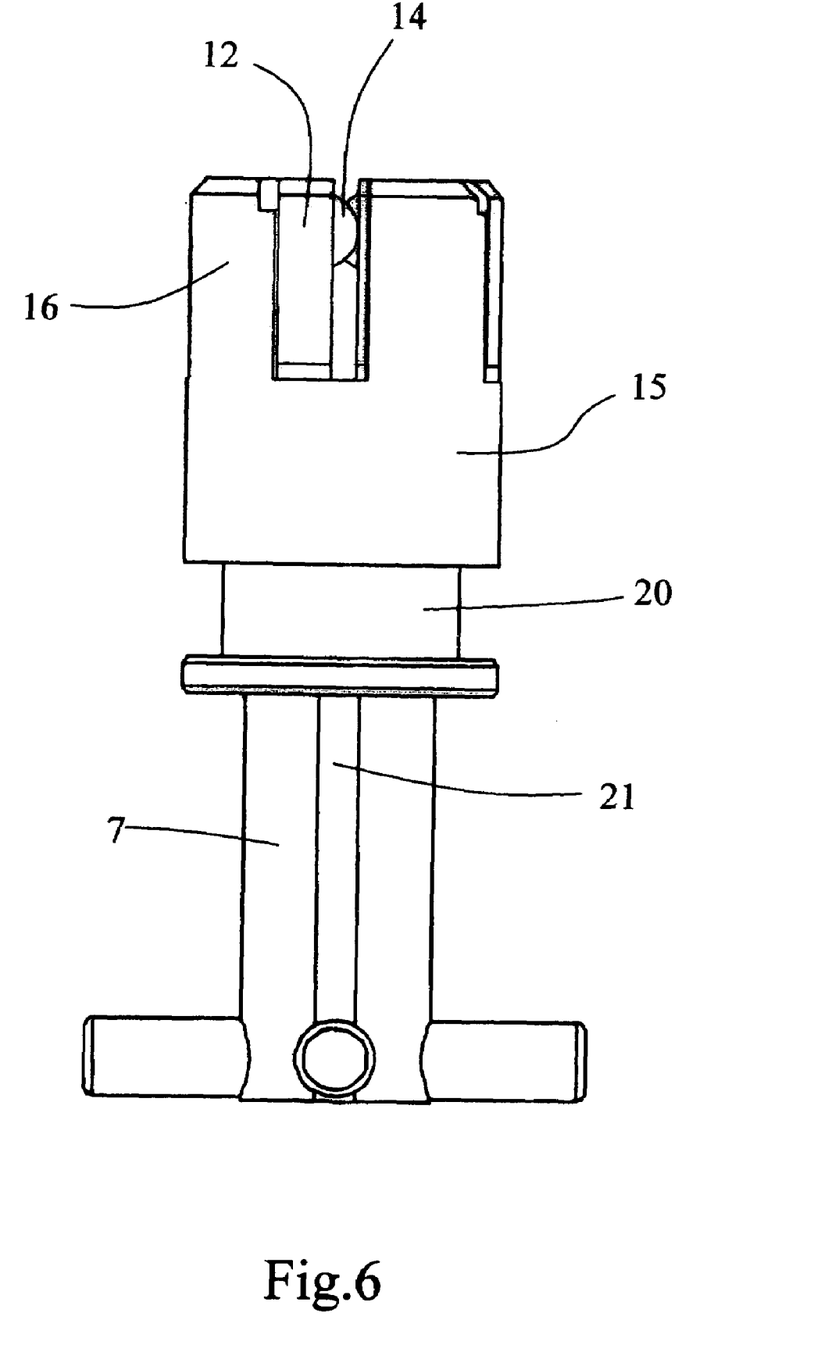
FIG. 6 is a side view of the adapter.

The ring 15 is held in this locking position by a spring 19 which rests on a supporting ring 20 which is mounted on the body 7 of the adapter, as shown in FIG. 4. In order to release the reamer all that must be done is pull out the locking ring 15 by constricting the spring 19, as shown in FIG. 5. The reamer can then be removed from the head 8 by pushing back the balls 14. The same method is used to fix the reamer onto the adapter. This type of locking/unlocking mode is described in the Swiss patent application No 409/00, the content of which is incorporated by reference herein. To lock the balls 14 into the reamer, all you have to do is release the ring 15.

In order to allow the adapter to be cleaned properly, the supporting ring 20 is mounted in such a way that it can be pulled out backwards as far as the cylindrical branches 9, which allows you to also bring back the locking ring 15 and to release the spring on the ring 15. For this purpose, the supporting ring 20 is fitted with a radial pin directed internally (not shown in the drawing) and the body 7 of the adapter has a longitudinal groove 21 into which this pin can slide. The upper end of the groove 21 leads to a notch 22 into which the pin on the ring 20 can be bayonet fixed by means of a slight rotation.

The reamer can usefully be fitted with a device allowing the shavings to be recovered. The plates offer a particularly simple and effective solution shown in FIGS. 9a, 9b and 10.

Figure 9A:
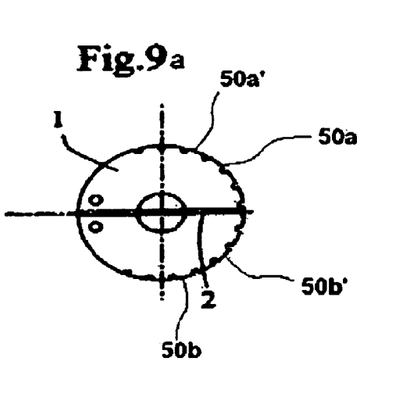
FIGS 9a–9b show a cup for recovering the shavings before being mounted on the reamer.
Figure 9B:
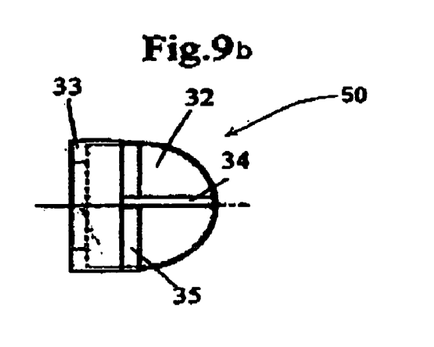
Figure 10:
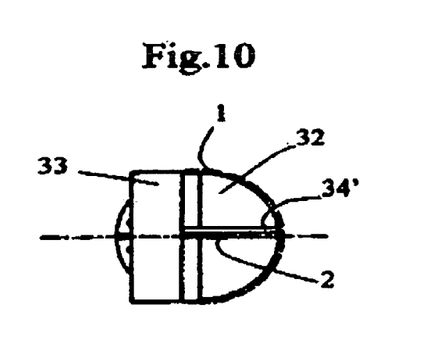
FIG. 10 shows the same cup mounted on the reamer.

The recovery devices are made up of a cup 32 in the shape of a hemispherical dome supported by a ring 33. The diameter of the cup 32 is slightly less than the diameter of the plates 1 and 2 and this cup has four splits 34 stretching according to the meridian levels at right angles to one another and over a part of the height of the ring 33, over a part 35 of the latter which has the same diameter as the cup 32. The width of the splits 34 is noticeably greater than the thickness of the plates 1 and 2 and these splits are asymmetrical in relation to the corresponding meridian plane, in such a way that when the cup 32 is mounted on the reamer (FIG. 10) the plates 1 and 2 cross the splits 34 leaving a split 34' behind the plates in relation to the reamer's direction of rotation, so as to allow the shavings to penetrate into the cup 32 through these splits 34'. It will be noted that the reamer plates shown in figures 9a and 9b and 10 are fitted with U-shaped teeth 50a, 50a', 50b, and 50b' which project over the surface of the cup 32.

Figure 11A:
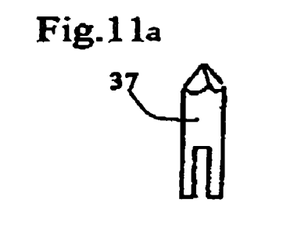
FIGS. 11a–11b show variants for point or centering stock production.
Figure 11B:
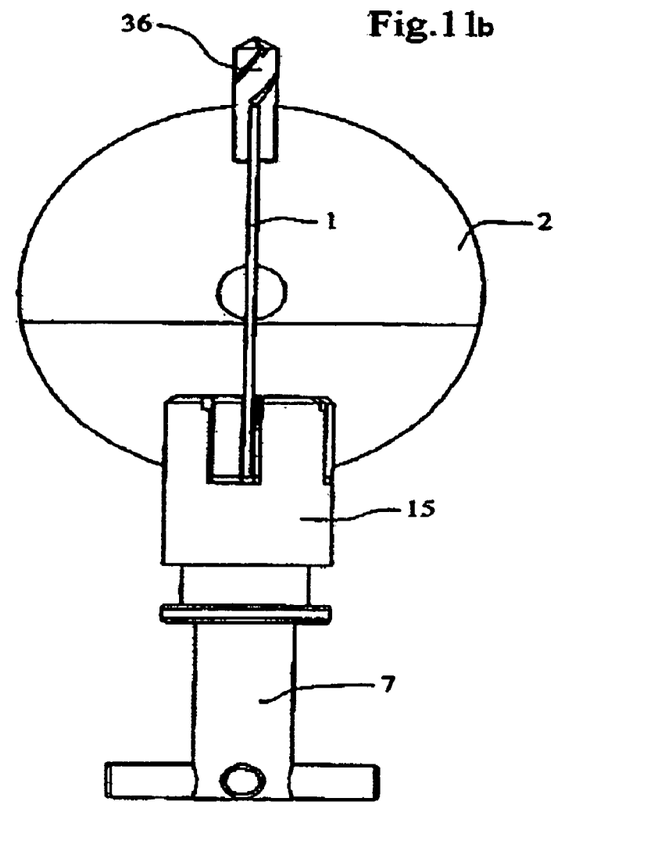

FIG. 11 illustrates a variation in which the two plates 1 and 2 are totally flat and form a cross at the end of the reamer. The reamer is fitted with a drill bit 36 fixed axially onto this cross. For this purpose, the bit 36 has two slots running crossways by means of which it is fitted onto the plates. The bit is laser welded onto the plates 1 and 2.

Instead of a bit, a simple centre point or a trocar point 37 could be fitted.

A drill bit or a point could be fixed in the same way onto a reamer made up of three, five or more plates.

Figure 12:
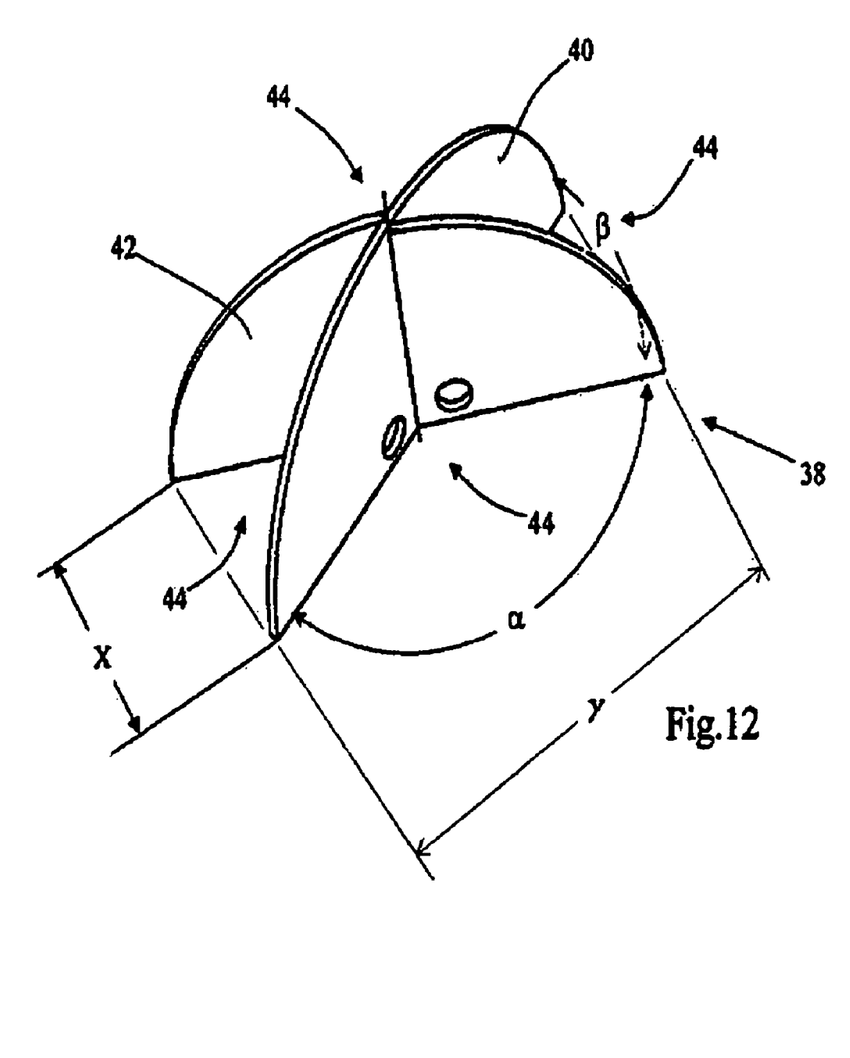
FIG. 12 shows an embodiment in which the plates are not equally spaced about the rotational axis.

FIG. 12 depicts an reamer 38 in which the plates 40 and 42 are spaced about the rotational axis so as to result in unequal spaces 44 between plates. The spaces 44 encompassed by angle β are smaller than the spaces encompassed by angle β, thus resulting in X and Y dimensions which are different.

Figure 13:
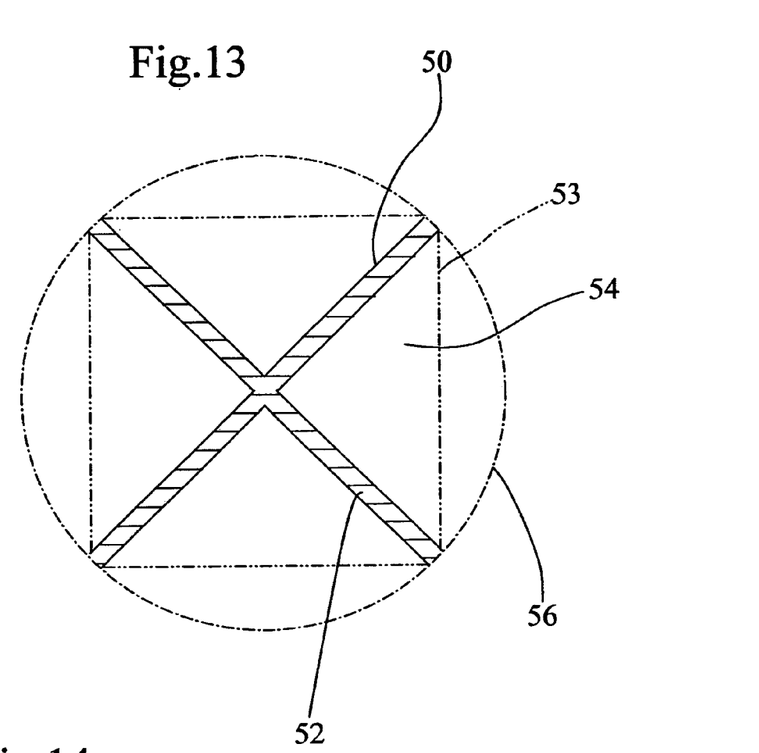
FIG. 13 shows the static profile area vs. the dynamic profile area of the invention.

FIG. 13 illustrates a cutting structure 50, made up of the two plates 1 and 2. When viewed statically and axially, the cutting structure 50 presents a two dimensional static profile area 52 in the form of a cross. The square 53 inscribed on the corners of this cross represents the minimum size of an incision which will allow passage of the reamer. The square 53 is therefore the effective profile seen by an incision upon insertion of the reamer into the bone socket and covers approximately 80% of the area of the circular profile area 54. When this static profile 52 is rotated during cutting, it sweeps out the circular profile area 54 inscribed by the phantom line circle 56.

Figure 14:
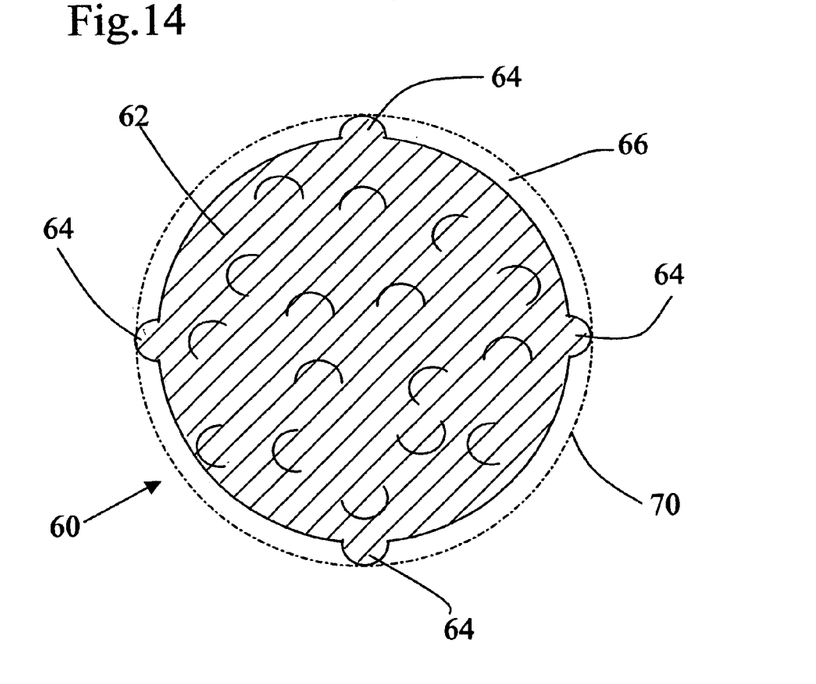
FIG. 14 shows the static profile area vs. the dynamic profile area of a prior art product.

FIG. 14 shows a conventional reamer 60, in which the static profile area 62 is essentially a circle with small protrusions 64 constituted of cutting divots. When rotated during cutting, the static profile area 62 sweeps out a dynamic profile area 66, inscribed by the phantom line 70, only insubstantially larger.

Thus, an advantage of having a substantially smaller static profile area 52 than dynamic profile area 54 is that the size of the incision required in order to receive the reamer is much smaller than that required for conventional reamers.

The invention is not limited to the modes of production described. Instead of the two fitted plates, the reamer could be made up of plates fixed radially on an axis, by means of welding, for instance. There do not have to be exactly four plates, but there must be at least one.

Whether these are plates fitted as shown or plates welded onto an axis, these plates could be of a different shape, for example a shape limited by a truncated or other form of case.

Although illustrative embodiments of the invention have been shown and described, a wide range of modification, change and substitution is contemplated in the foregoing disclosure and in some instances, some features of the present invention may be employed without a corresponding use of the other features. Accordingly, it is appropriate that the appended claims be construed broadly and in a manner consistent with the scope of the invention.

What is claimed is:

1. A surgical reamer for cutting a bone socket, comprising,
a cutting structure (50) which comprises at least two plates (1, 2) rotatable about a rotational axis and mounted so as to traverse the rotational axis, the cutting structure having a static profile area (52) upon insertion of the reamer into the bone socket and a dynamic profile area (56, 70) generated upon rotation, both profile areas lying transverse to the axis,
wherein the static profile area is circumscribed by a nonequilateral, substantially rectangular area (53) in which a lateral width (X) of the rectangular area is substantially smaller than a longitudinal width (Y) of the rectangular area and in which the static profile area is substantially smaller than the dynamic profile area.

2. The surgical reamer of claim 1 wherein the reamer is adapted to be mounted to a tool holder for controlled rotational motion.

3. The surgical reamer of claim 1 wherein the dynamic profile area is a circular area.

4. The reamer of claim 1 wherein at least one plate of the cutting structure (50) has an edge adapted to cut bone.

5. The reamer of claim 4 wherein the static profile area has a flattened X-shape.

6. The reamer of claim 1 wherein the static profile area (52) is no greater than about 80 percent of an inscribed circular area (56, 70).

7. The reamer as in claim 1, wherein the cutting structure (50) has at least one cutting edge fitted with teeth (FIGS. 7a, b, c).

8. The reamer of claim 1 wherein the two plates (1, 2) are split down the middle along their axis of symmetry, and fixed to one another.

9. The reamer of claim 1, wherein the plates (1, 2) are in the shape of disks.

10. The reamer of claim 1, fitted with a bit (36) or a centre point or a trocar point (37) attached to the plates (1, 2) coaxial with the rotational axis of the reamer.

11. The reamer of claim 1, including a device for recovering shavings (32).

12. The surgical reamer of claim 1, wherein the plates (1,2) of the cutting structure (50) are releasably connected to the reamer so as to permit quick attachment and removal thereof.

13. An acctabular reamer comprising,
a support structure (50) comprising at least two plates (1, 2) rotatable about a rotational axis and mounted so as to traverse the rotational axis, the plates defining a cutting structure (50), presenting a plurality of cutting edges, the support structure further defining a static profile area (52) upon insertion into the bone and a dynamic profile area (56, 70) which is circular, the dynamic profile area being generated upon rotation, both profile areas being transverse to the axis,
wherein the static profile area is circumscribed by a non-equaliateral, rectangular area (53) in which a lateral width (X) of the rectangular area is substantially smaller than a longitudinal width (Y) of the rectangular area and in which the static profile area is substantially smaller than the dynamic profile area.

14. The surgical reamer of claim 13 wherein the reamer is adapted to be mounted to a tool holder for controlled rotational motion.

15. The reamer of claim 14 wherein the static profile area has a flattened X-shape.

16. The reamer of claim 13 wherein at least one plate has an edge adapted to cut bone.

17. The reamer of claim 13 wherein the static profile area is no greater than about 80 percent of the dynamic profile area.

18. The surgical reamer of claim 13, wherein the plates (1,2) of the cutting structure (50) are releasably connected to the reamer so as to permit quick attachment and removal thereof.

19. A surgical reamer for cutting a bone socket, comprising two intersecting plates (1, 2) define a cutting structure (50), rotatable about a rotational axis (X—X) when mounted to a holder (6), the plates sweeping a circular cutting profile area (54) when rotated axially with the holder, wherein the plates present a two dimensional static profile area (52) in the form of a flattened X which is circumscribed by a nonequilateral, rectangular area (53) in which a lateral width (X) of the rectangular area is substantially smaller than a longitudinal width (Y) of the rectangular area and in which the static profile area is substantially smaller than the circular cutting profile area (54), wherein the plates have a holder interface (18) centrally located with the rotational axis, permitting the holder to have a small outside dimension so that when the holder and reamer are attached to each other in an assembled arrangement, the holder may sweep out a diametral area substantially smaller than the circular cutting profile area (56, 70), thus permitting a substantially smaller incision for entry of the reamer into a body.

20. The reamer of claim 19, wherein the holder interface comprises a hole (18) in the plate allowing the reamer to be fixed onto a tool holder or an adapter (6).

21. The reamer of claim 19, wherein the plate (1,2) has a circular cut (3) in which a cup for recovering shavings is housed.

22. The surgical reamer of claim 19, wherein the plates (1,2) of the cutting structure (50) are releasably connected to the reamer so as to permit quick attachment and removal thereof.

23. A surgical reamer for cutting a bone socket, comprising,
a cutting structure (50) which comprises at least two plates (1, 2) rotatable about a rotational axis and mounted so as to traverse the rotational axis, the cutting structure having a static profile area (52) upon insertion of the reamer into the bone socket and a dynamic profile area (56, 70) generated upon rotation, both profile areas lying transverse to the axis,
wherein the static profile area is substantially smaller than the dynamic profile area, and, wherein the cutting structure (50) has at least two cutting edges (50a, 50b) each having corresponding teeth (50a', 50b'), the teeth of one edge being offset in relation to the teeth of another edge according to the trajectory of the teeth.

24. The surgical reamer of claim 23, wherein the plates (1,2) of the cutting structure (50) are releasably connected to the reamer so as to permit quick attachment and removal thereof.

25. A surgical reamer for cutting a bone socket, comprising,
a cutting structure (50) which comprises at least two plates (1, 2) rotatable about a rotational axis and mounted so as to traverse the rotational axis, the cutting structure having a static profile area (52) upon insertion or the reamer into the bone socket and a dynamic profile area (56, 70) generated upon rotation, both profile areas lying transverse to the axis,
wherein the static profile area is substantially smaller than the dynamic profile area,
wherein the two plates (1, 2) are split down the middle along their axis of symmetry, and fixed to one another, and,
wherein the split of the plate (1) extends to the top of the reamer and is cut so that its sides diverge from one another on the plane of the other plate, on both sides of the rotational axis of the reamer.

26. The surgical reamer of claim 25, wherein the plates (1,2) of the cutting structure (50) are releasably connected to the reamer so as to permit quick attachment and removal thereof.

27. A surgical reamer for cutting a bone socket, comprising,
a cutting structure (50) which comprises at least two plates (1, 2) rotatable about a rotational axis and mounted so as to traverse the rotational axis, the cutting structure having a static profile area (52) upon insertion of the reamer into the bone socket and a dynamic profile area (56, 70) generated upon rotation, both profile areas lying transverse to the axis,
wherein the static profile area is substantially smaller than the dynamic profile area, and
wherein the reamer includes a device for recovering shavings made up of a cup (32) located at the centre of the roamer.

28. The reamer of claim 27, wherein the cup (32) is in the shape of a dome fitted with diametric slots (34) traversed by the plates (1, 2).

29. The surgical reamer of claim 27, wherein the plates (1,2) of the cutting structure (50) are releasably connected in the reamer so as to permit quick attachment and removal thereof.

30. A surgical reamer for shaping a bone socket in a patient, comprising:
a cutting structure (50) comprising at least two plates rotatable about a rotational axis and mounted so as to traverse the rotational axis, the cutting structure defining a shape with a static profile (52) transverse to the axis upon insertion of the reamer into the patient, and another shape with a dynamic profile (56, 70) generated upon rotation or the structure within the socket, wherein the static profile is substantially smaller than the dynamic profile and wherein the static profile is circumscribed by a non-equilateral, substantially rectangular area (53).

31. The surgical reamer of claim 30, wherein the plates (1,2) of the cutting structure (50) are releasably connected to the reamer so as to permit quick attachment and removal thereof.

* * * * *

UNITED STATES PATENT AND TRADEMARK OFFICE
CERTIFICATE OF CORRECTION

| | | |
|---|---|---|
| PATENT NO. | : 7,011,662 B2 | Page 1 of 1 |
| APPLICATION NO. | : 10/450771 | |
| DATED | : March 14, 2006 | |
| INVENTOR(S) | : Lechot et al. | |

It is certified that error appears in the above-identified patent and that said Letters Patent is hereby corrected as shown below:

Column 1 after title on line 1, add the following header and paragraph:

-- CROSS REFERENCE TO RELATED APPLICATIONS
This application is the national stage entry of PCT/IB01/02676, filed December 21, 2001, which claims priority to CH 2500/00, filed December 21, 2000. --

Signed and Sealed this
Eighteenth Day of September, 2012

David J. Kappos
*Director of the United States Patent and Trademark Office*